(12) United States Patent
Aizawa et al.

(10) Patent No.: US 7,214,177 B2
(45) Date of Patent: May 8, 2007

(54) CULTURE TUBE AND ANGLE ROTOR RECEIVING THE TUBE IN CENTRIFUGE

(75) Inventors: Masaharu Aizawa, Hitachinaka (JP); Masataka Morita, Hitachinaka (JP)

(73) Assignee: Hitachi Koki Co., Ltd., Tokyo (JP)

( * ) Notice: Subject to any disclaimer, the term of this patent is extended or adjusted under 35 U.S.C. 154(b) by 184 days.

(21) Appl. No.: 10/422,852

(22) Filed: Apr. 25, 2003

(65) Prior Publication Data

US 2003/0203800 A1 Oct. 30, 2003

(30) Foreign Application Priority Data

Apr. 26, 2002 (JP) ............................ P2002-126586
Apr. 9, 2003 (JP) ............................ P2003-105177

(51) Int. Cl.
*B04B 5/02* (2006.01)
(52) U.S. Cl. ........................................ 494/16; 215/354
(58) Field of Classification Search ................. 494/16, 494/33, 85; 422/102; 220/288; 215/354, 215/305, 320, 329
See application file for complete search history.

(56) References Cited

U.S. PATENT DOCUMENTS

| | | | | |
|---|---|---|---|---|
| 2,813,650 | A | * | 11/1957 | Takahashi et al. ........... 215/305 |
| 2,965,256 | A | * | 12/1960 | Yochem ..................... 215/329 |
| 3,366,320 | A | * | 1/1968 | Cho ............................ 494/16 |
| 3,456,876 | A | * | 7/1969 | McEwen ..................... 494/16 |
| 3,540,612 | A | * | 11/1970 | Brady ........................ 215/329 |
| 3,881,627 | A | * | 5/1975 | Davolt ....................... 215/329 |
| 4,469,235 | A | * | 9/1984 | Parker ........................ 215/295 |
| 4,537,320 | A | * | 8/1985 | Nielsen ....................... 215/276 |
| 4,690,670 | A | * | 9/1987 | Nielsen ......................... 494/16 |
| 5,100,013 | A | * | 3/1992 | Strassheimer ............... 215/354 |
| 5,213,225 | A | * | 5/1993 | King et al. .................. 215/330 |
| 5,358,129 | A | * | 10/1994 | Watts ........................ 215/206 |
| 5,460,283 | A | * | 10/1995 | MaCartney et al. ......... 215/270 |
| 5,672,321 | A | * | 9/1997 | Daykin ....................... 422/102 |
| 5,916,525 | A | * | 6/1999 | Husar et al. ................. 422/102 |
| 6,702,134 | B2 | * | 3/2004 | Scalese et al. .............. 215/344 |
| 7,004,898 | B2 | * | 2/2006 | Hara ........................... 494/16 |

FOREIGN PATENT DOCUMENTS

| | | | |
|---|---|---|---|
| JP | 5-9653 U | | 2/1993 |
| JP | 7-151661 A | | 12/1994 |
| JP | 9-299813 A | | 11/1997 |
| JP | 2004-49970 | * | 2/2005 |
| JP | 2004-188346 | * | 7/2005 |

* cited by examiner

*Primary Examiner*—Charles E. Cooley
(74) *Attorney, Agent, or Firm*—Sughrue Mion, PLLC

(57) ABSTRACT

A culture/centrifugal tube includes a tube and a cap. The cap has a disk portion and an annular portion that define an annular groove therebetween. The annular groove opens at a position level with the surface of the disk portion. The open end of the tube extends into the annular groove, with the open end of the vessel in abutment against the surface of the disk portion when the cap is fully engaged on the tube. An angle rotor that is used in a centrifuge is formed with an accommodation hole that receives the culture/centrifugal tube. The accommodation hole including a smaller-diameter tube accommodating portion that accommodates the tube and a larger-diameter cap accommodating portion that accommodates the cap. The cap accommodating portion includes a region that entirely encompasses a corresponding portion of the outer periphery of the annular portion of the cap.

13 Claims, 7 Drawing Sheets

(12) United States Patent

CULTURE TUBE AND ANGLE ROTOR RECEIVING THE TUBE IN CENTRIFUGE

BACKGROUND OF THE INVENTION

1. Field of the Invention

The present invention relates to an angle rotor and a culture/centrifugal tube used in the angle rotor.

2. Description of Related Art

High-speed centrifuges are available in small sizes and with cooling functions and are used in a variety of fields, such as the medical, chemical, pharmaceutical, and genetic engineering fields. Disposable culture centrifuge tubes are used in the centrifuges.

One type of centrifuge includes an angle rotor and a motor that produces drive force that rotates the angle rotor. A culture centrifuge tube filled with a sample liquid to be separated is mounted in the angle rotor, and the motor rotates the angle rotor. This type of centrifuge can rotate at maximum speeds of 5,000 to 14,000 RPMs. Some centrifuges can reach maximum speeds of up to 25,000 RPMs. Angle rotors are produced for various uses and are rotated either under atmospheric pressure or within a vacuum.

Here are some examples of angle rotor models on the market today: R12A5, R10A2, T11A21, and T9A31 produced by Hitachi Koki Co., Ltd. and TA22 and TA23 produced by Tomy Digital Biology Co., Ltd. These angle rotors are normally made from an aluminum alloy. To produce an angle rotor, a block of the aluminum alloy is machined with accommodation holes for accommodating the culture centrifuge tubes and with a drive shaft hole for inserting the drive shaft of the drive motor.

Culture centrifuge tubes supported in the angle rotor are sample tubes used in centrifugal separation and are alternatively referred to as culture/centrifugal tubes, tissue culture/centrifugal tubes, centrifugal tubes, or tissue culture/centrifugal tubes (TC tubes). A variety of culture/centrifugal tubes, such as those produced by Sumitomo Bakelite Co., Ltd., Asahi Technoglass Corporation, and KK Ashisato, are on the market. Culture centrifugal tubes, including the cap, are made from a plastic material such as polypropylene or polystyrene using injection technology. Because culture/centrifugal tubes are disposable and used in large quantities, they need to be inexpensive. The culture/centrifugal tubes are used as a container for cell culture and then inserted in the angle rotor as is to collect the cultivated cells.

FIG. 1 shows a configuration of a conventional angle rotor 101. The angle rotor 101 is driven by a motor (not shown) to rotate around a rotation axis B—B. The angle rotor 101 is formed with an accommodation hole 110a that slants at a predetermined angle with respect to the rotation axis B—B. The accommodation hole 110a is for accommodating a culture/centrifugal tube 120. As will be described later, the culture/centrifugal tube 120 is for use in a centrifuge and includes a tube 121 and a cap 122. The accommodation hole 110a includes a tube accommodation portion 110f and a step 110g. The tube accommodation portion 110f and the step 110g are continuous with each other. The tube accommodation portion 110f accommodates the tube 121 and the step 100g accommodates the cap 122.

As shown in FIG. 2, the culture/centrifugal tube 120 includes the tube 121 and the cap 122. The tube 121 and the cap 122 are made from plastic. One end of the tube 121 is closed and defines a bottom 121A. The other end defines an opening portion 121B. A spiral-shaped male screw portion 121C is formed near the opening portion 121B. The cap 122 is provided for covering the opening portion 121B and includes a disk portion 122A and an annular portion 122B. The annular portion 122B extends from the outer periphery of one surface 122C of the disk portion 122A in the axial direction of the disk portion 122A. The inner peripheral surface of the annular portion 122B is formed with a spiral-shaped female screw portion 122F. An annular lip 122J extends from the surface 122C of the disk portion 122A. The annular lip 122J has a smaller diameter than the outer periphery of the disk portion 122A.

The cap 122 is placed over the opening portion 121B of the tube 121 and twisted to engage the male screw 121C with the female screw 122F. By this, the cap 122 covers the opening portion 121B of the tube 121 with the annular lip 122J of the cap 122 in intimate contact with the opening portion 121B. Therefore, the cap 122 seals the opening portion 121B of the tube 121. As shown in FIG. 1, the culture/centrifugal tube 120 is then inserted into the accommodation hole 110a of the angle rotor 101. Centrifugal separation is then performed by rotating the angle rotor 101.

As shown in FIG. 2, the male screw 121C of the tube 121 is provided at a position that is separated from an open end 121E of the opening portion 121B. Also, the female screw portion 122F is provided at a position that is separated from the position where the annular portion 122B and the disk portion 122A of the cap 122 are connected to each other. Accordingly, a space 122f is formed at the position near the open end 121E of the tube 121 and the position near where the annular portion 122B and the disk portion 122A of the cap 122 are connected to each other. Neither the male screw 121C nor the female screw portion 122F are located in the space 122f and the cap 122 and the tube 121 are separated from each other at the space 122f.

FIG. 3 shows a culture/centrifugal tube 120 with a cap 122' that is shaped differently from the cap 122 shown in FIG. 2. The cap 122' includes a disk portion 122A' and an annular protrusion 122J'. The annular protrusion 122J' extends from one surface 122C' of the disk portion 122A'. When the opening portion 121B of the tube 121 is covered by the cap 122', the annular protrusion 122J' comes into intimate contact with the opening portion 121B of the tube 121 and seals the opening portion 121B of the tube 121.

Japanese Patent-application Publication Nos. 9-299813 and 7-151661 and Japanese Utility-model Publication No. 5-9653 disclose technology related to culture/centrifugal tubes. In particular, Japanese Patent-application Publication No. 9-299813 discloses a container used for dialysis purposes. The container has an accommodation body and a lid that can be freely attached to and detached from each other by screws provided on their inner and outer peripheral surfaces. Japanese Patent-application Publication No. 7-151661 discloses a phase separation tube having an opening portion at both ends. Japanese Utility-model Publication No. 5-9653 discloses a method of producing a plastic tube in a sealed condition. First, a tube that is to be processed into the container portion is formed with a taper shape at the outer peripheral surface of the opening end. A plug is inserted into the open end of the tube to make an intimate seal.

SUMMARY OF THE INVENTION

The time required for centrifugal separation is inversely proportional to the centrifugal acceleration of the angle rotor. Therefore, the time required for centrifugal separation may be shortened by increasing the centrifugal separation rotational speed and increasing the centrifugal acceleration. Generally, cultured cells can be subjected to a load of up to 50,000 g without losing virility or dying. Therefore, it is conceivable to reduce the time required for centrifugal separation by increasing the centrifugal separation rotational speed to produce a load of about 50,000 g.

The cap 122 and the opening portion 121B of the conventional culture/centrifugal tube 120 have low rigidity and strength. Further, the accommodation hole 110a of the angle rotor 101 does not sufficiently support the culture/centrifugal tube 120 during centrifugal separation. For these reasons, if the rotational speed of the angle rotor 101 is increased, then the opening portion 121B of the tube 121 can deform or the cap 122 can separate from the opening portion 121B. The inventors performed experiments using a commercially available culture/centrifugal tube in the R12A5 model angle rotor produced by Hitachi Koki Co., Ltd. and rotating the angle rotor at about 15,000 revolutions per minute to produce a centrifugal force of about 30,000 g. As shown in FIG. 4, the opening portion 121B of the tube 121 deformed under centrifugal force and the cap 122 separated from the tube 121.

Here, this problem will be discussed in more detail. The culture/centrifugal tube 120 has a liquid sample 103 in it before centrifugal separation begins. As shown in FIG. 4, the liquid sample 103 shifts to the outermost side of the culture/centrifugal tube 120 during centrifuging. Because the cap 122 seals the tube 121 with only a poor-seal, the amount of liquid sample 103 in the culture/centrifugal tube 120 is limited to a predetermined amount, so that the liquid sample 103 will not reach the cap 122 or the opening portion 121B of the tube 121 during centrifuging, even if during centrifugal separation the liquid sample 103 shifts to the outermost side of the culture/centrifugal tube 120 until its surface is oriented substantially vertically as shown in FIG. 4.

That is, the culture/centrifugal tube 120 only requires a seal sufficient to prevent leaks when the culture/centrifugal tube 120 is filled with a sample liquid and cultivated in a shaking incubator or when a technician handles the culture/centrifugal tube 120. Accordingly, the seal produced by intimate contact between the opening portion 121B and the lip 122J shown in FIG. 2 and the protrusion portion 122J' shown in FIG. 3 is merely a seal produced by contact between two plastic surfaces, and is not sufficient for withstanding high pressures in the manner of an O-ring, for example. The predetermined amount of the liquid sample 103 was set as described above to prevent the liquid sample 103 from reaching the opening portion 121B and leaking out.

When the angle rotor 101 rotates at a high speed, then centrifugal acceleration operates on the liquid sample 103, the tube 121, and the cap 122. As the centrifugal force operates on the liquid sample 103, the liquid sample 103 applies pressure to the inner peripheral surface of the tube 121 so that the tube 121 expands where the liquid sample 103 is located. At this time, the wall of the accommodation hole 110a supports the portions of the tube 121 that are located in the accommodation hole 110a. Therefore, these portions do not greatly deform or become crushed by the centrifugal force. Although the liquid sample 103 is not located in the opening portion 121B so no pressure from the liquid sample 103 operates no the opening portion 121B, the opening portion 121B itself moves under the centrifugal force radially away from the rotational axis B—B and deforms as shown in FIG. 4. The cap 122 deforms in the same manner as the opening portion 121B, that is, the cap 122 itself moves under centrifugal force radially away from the rotational axis B—B and deforms.

The step 110g of the conventional angle rotor 101 does not encompass the cap 122 around the entire periphery of the cap 122. Therefore, the non-encompassed side (right side in FIG. 4) can lift up. Therefore the conventional angle rotor 101 does not sufficiently prevent the cap 122 from moving and deforming. For this reason, when the cap 122 deforms in the above-described manner, the lip portion 122J and the opening portion 121B cannot be maintained in intimate contact so that the seal cannot be maintained.

There are also conventional angle rotors that are not formed with a step. In this case, centrifuging is performed with the cap 122 in a suspended condition, that is, without any support.

The angle rotor 101 that accommodates the conventional culture/centrifugal tube 120 cannot be used at a high centrifugal acceleration so it has been difficult to speed up centrifuging process and processes that include centrifuging separation of the liquid sample 103.

It is an objective of the present invention to overcome the above-described problems and to provide a culture/centrifugal tube that is inexpensive, easy to handle, has high rigidity and strength, and that can withstand high centrifugal acceleration, and an angle rotor that supports the cap of the culture/centrifugal tube during centrifugal separation by high speed rotation and prevents the cap and the opening portion of the tube from deforming.

In order to achieve the above-described objectives, a culture/centrifugal tube according to the present invention is used to hold a sample liquid and inserted into an accommodation space in an angle rotor of a centrifuge. The angle rotor rotates to subject the culture/centrifugal tube to centrifugal force. The culture/centrifugal tube includes a plastic vessel and a plastic cap.

The plastic vessel includes a base end, an open end, and a side wall. The base end is closed. The open end is open and opposite from the base end. The open end has an outer periphery and a rim. The outer periphery is formed with a spiral-shaped male screw and the rim defines an opening. The side wall extends between the base end and the open end. The side wall and the base end define an inside of the plastic vessel.

The plastic cap is for covering the opening of the vessel. The cap includes a disk portion and an annular portion. The disk portion has a bottom surface and an outer peripheral surface. The bottom surface faces downward and has a perimeter. The outer peripheral surface extends upwardly from the perimeter of the bottom surface. The annular portion is connected to a portion of the outer peripheral surface of the disk portion and extends downward. The annular portion has an inner peripheral surface formed with a spiral-shaped female screw that engages with the male screw of the vessel to seal the inside of the vessel.

Moreover, an annular groove is defined between the annular portion and the outer peripheral surface of the disk portion. The annular groove extends downward and opens at a position level with the bottom surface of the disk portion. The open end of the vessel extends into the annular groove with the open end of the vessel in abutment against the disk portion when the male screw and the female screw are fully engaged.

An angle rotor according to the present invention is for receiving the above-described culture/centrifugal tube and used in a centrifuge. The centrifuge has a motor that generates force for rotating the angle rotor and subjecting the culture/centrifugal tube to centrifugal force. The angle rotor includes a connection member and an accommodation portion. The connection member is for connecting to the motor of the centrifuge. The accommodation portion is rotated about a rotation axis through the connection member by the drive force from the motor. The accommodation portion includes an accommodation hole forming portion that defines an accommodation hole accommodating the culture/centrifugal tube. The accommodation hole extends in a direction at an angle to the rotation axis. The accommodation hole forming portion includes a vessel accommodating portion that accommodates the vessel and a cap accommodating portion that accommodates the cap. The vessel accommodating portion has a smaller diameter than the cap accommodating portion. The cap accommodating portion includes a region that extends a predetermined distance in the direction. The region entirely encompasses a corresponding portion of the outer periphery of the annular portion of the cap.

BRIEF DESCRIPTION OF THE DRAWINGS

The above and other objects, features and advantages of the invention will become more apparent from reading the following description of the preferred embodiments taken in connection with the accompanying drawings in which.

DETAILED DESCRIPTION OF THE PREFERRED EMODIMENTS

Figure 1:
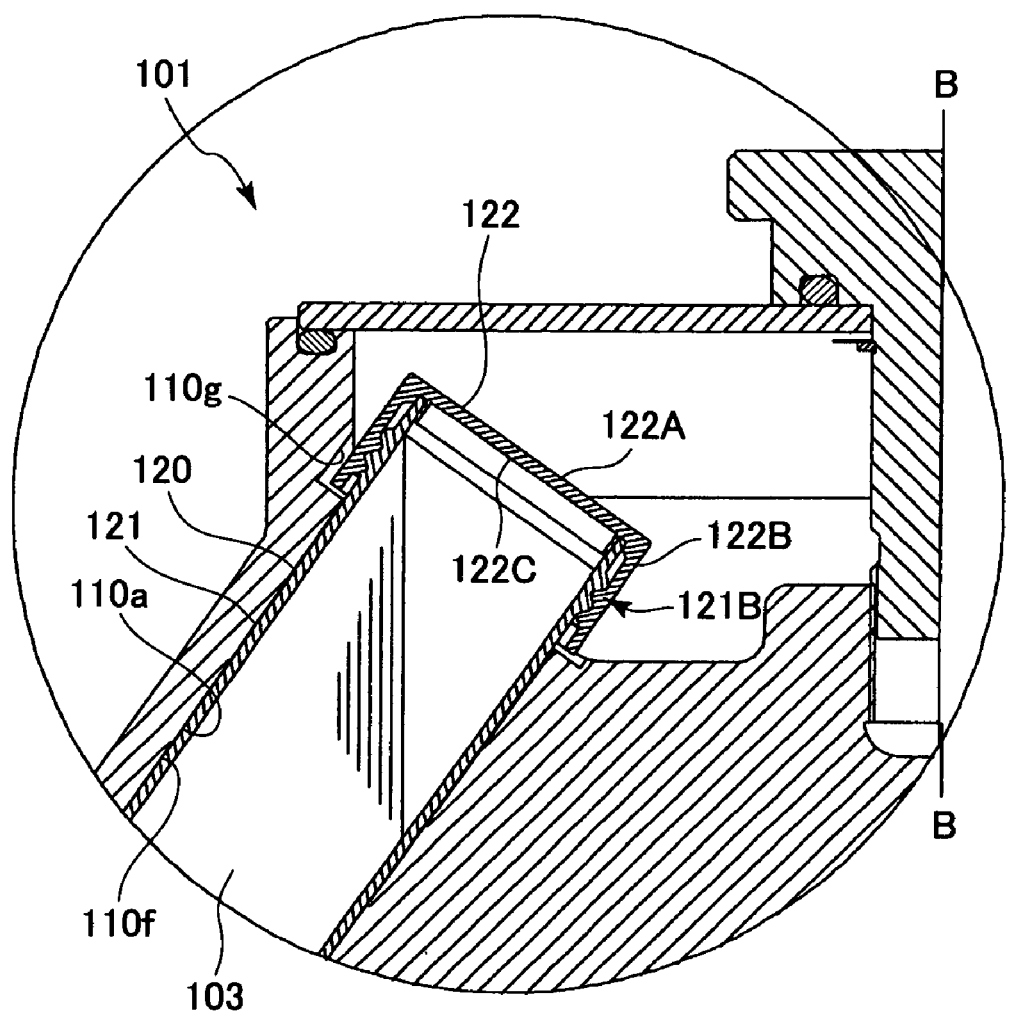
FIG. 1 is a cross-sectional view showing a conventional culture centrifuge tube inserted in a conventional angle rotor of a centrifuge.

Next, a culture/centrifugal tube and an angle rotor according to an embodiment of the present invention will be described with reference to FIGS. 5 through 9. As shown in FIG. 1, an angle rotor 1 according to the present embodiment includes a rotor body 10, a cover 11, and a handle 12. The angle rotor 1 is provided in a centrifuge. The handle 12 is for attaching the cover 11 to the rotor body 10.

Figure 5:
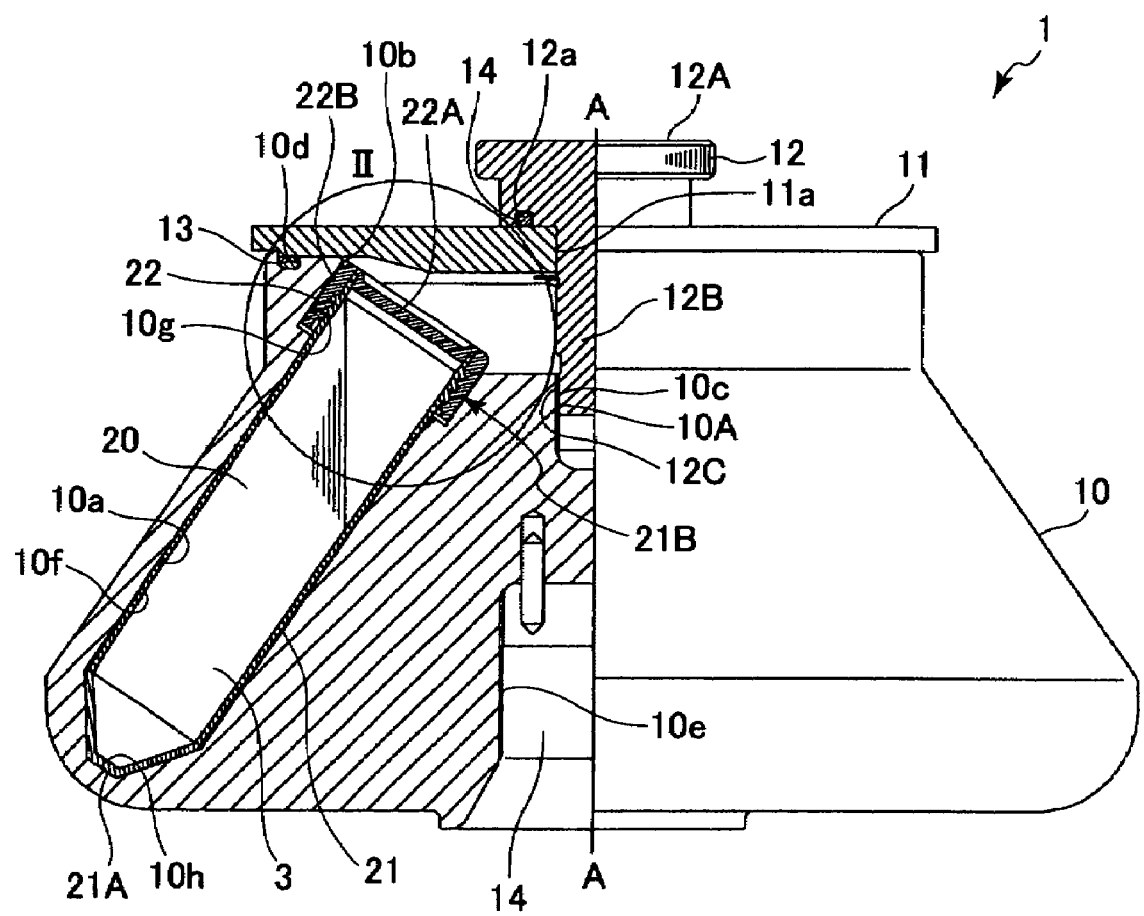
FIG. 5 is a side view partially in cross-section showing a culture centrifuge tube according to an embodiment of the present invention inserted in an angle rotor according to the embodiment.
Figure 7:
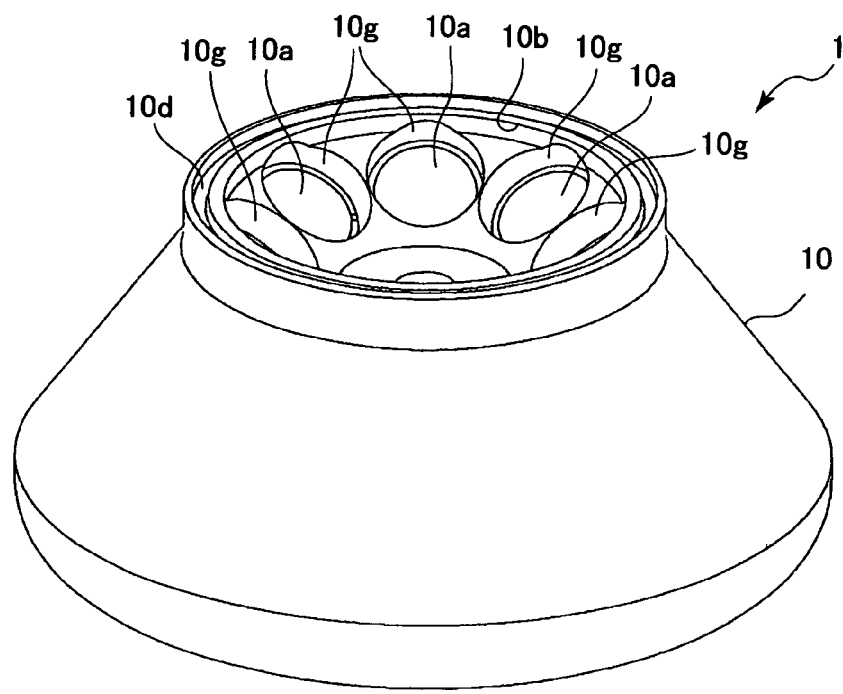
FIG. 7 is perspective view showing the angle rotor of FIG. 5.

The rotor body 10 is connected to a motor (not shown) that is provided in the centrifuge. The motor drives the rotor body 10 to rotate about a rotation axis A—A. As shown in FIG. 7, the rotor body 10 is formed with a plurality of accommodation holes 10a disposed equidistance around the rotational axis A—A. As can be seen in FIG. 5, each of the accommodation holes 10a extends radially and downward from the rotational axis A—A to define a predetermined angle with respect to the rotational axis A—A. In other words, the distance between the rotational axis A—A and the accommodation holes 10a in the radial direction increases, the further downward along the rotational axis A—A.

An opening portion 10b is formed in the upper portion of the rotor body 10. The accommodation holes 10a are brought into communication with atmosphere through the opening portion 10b. As shown in FIG. 5, a handle engagement hole 10c is formed in the upper portion of the rotor body 10 so as to follow the rotational axis A—A of the rotor body 10 downward. A spiral-shaped female screw 10A is formed in the inner peripheral surface of the handle engagement hole 10c. An annular groove 10d is formed in the upper portion of the rotor body 10. An O-ring 13 is fitted in the annular groove 10d and serves as a seal member. A drive shaft hole 10e is formed in the lower portion of the rotor body 10 so as to follow the rotational axis A—A of the rotor body 10 upward. A drive shaft 14, which can be connected to the drive motor (not shown), is engagable in the drive shaft hole 10e.

The accommodation holes 10a are formed to match the outer contour of a culture/centrifugal tube 20 (to be described later) so that the culture/centrifugal tube 20 can be inserted into any of the accommodation holes 10a. Each of the accommodation holes 10a includes a tube accommodation portion 10f and a cap accommodation portion 10g. The tube accommodation portion 10f is a tube-shaped hole with relatively small diameter for accommodating and supporting a tube portion 21 of the culture/centrifugal tube 20. The cap accommodation portion 10g is a tube-shaped hole with relatively large diameter for accommodating and supporting a cap 22 of the culture/centrifugal tube 20.

The cover 11 has a substantially disk shape and is capable of closing the opening portion 10b during centrifugal separation. A through hole 11a is formed in the substantial center of the cover 11. The handle 12 is inserted into the through hole 11a. The handle 12 includes a flange 12A at one end and a shaft 12B at the other end. The flange 12A has a cylindrical shape and is positioned at one side of (above) the cover 11. The shaft 12B forms all portions of the handle 12 other than the flange 12A. The shaft 12B extends into the through hole 11a of the cover 11 and through to the other side of (below) the cover 11. An annular groove 12a is formed in the flange 12A and confronts the cover 11. An O-ring 14 is fitted into the annular groove 12a. A male screw 12C is formed in the handle 12 at a position near the lower end of the handle 12.

When centrifugal separation is to be performed, the culture/centrifugal tube 20 is inserted into one of the accommodation holes 10a. Then, the male screw 12C of the handle 12 is screwingly engaged with the female screw 10A of the handle engagement hole 10c until the cover 11 abuts the O-ring 13 of the rotor body 10. At this time, the O-ring 14 abuts against the cover 11. As a result, the cover 11 is fixed to the rotor body 10 and the O-rings 13, 14 completely block fluid communication between the accommodation holes 10a and atmosphere.

Figure 8:
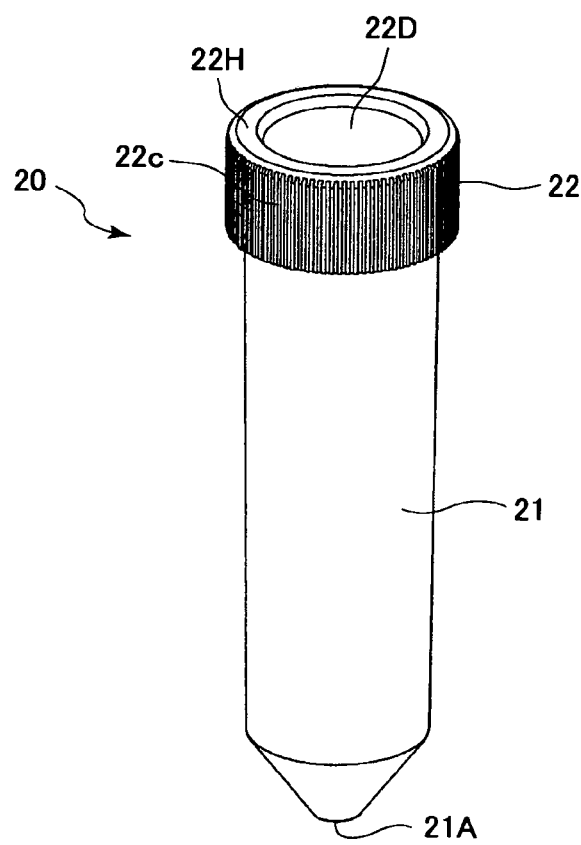
FIG. 8 is a perspective view showing the culture centrifuge tube of FIG. 5.
Figure 9:
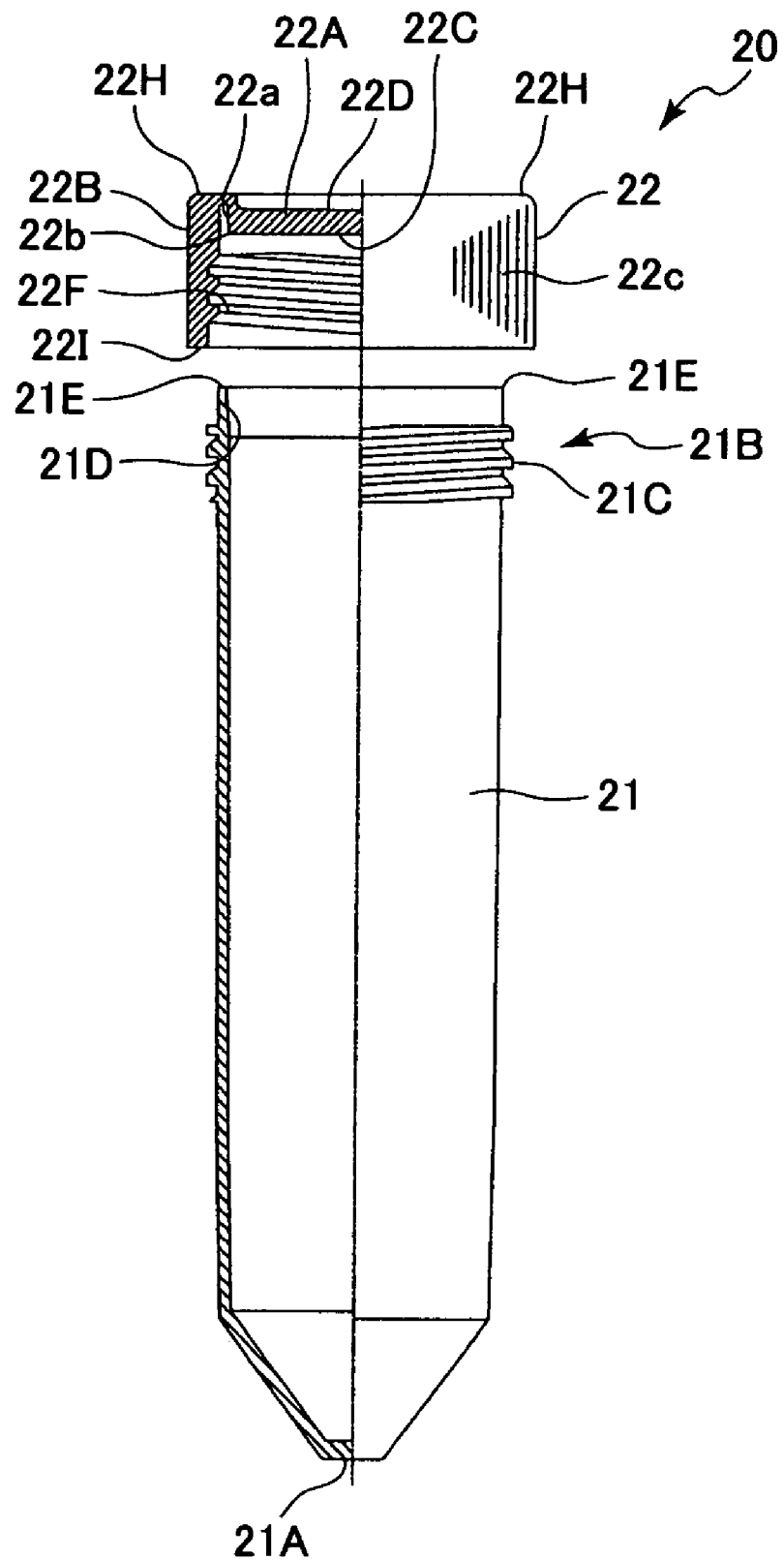
FIG. 9 is a side view partially in cross-section showing the culture centrifuge tube of FIG. 8.

Next, an explanation will be provided for the culture/centrifugal tube 20, which is inserted into and accommodated in the accommodation holes 10a of the angle rotor 1. As shown in FIGS. 8 and 9, the culture/centrifugal tube 20 includes the tube portion 21 and the cap 22. The tube portion 21 and the cap 22 are both made from polycarbonate using injection technology. The tube portion 21 has a tubular shape. One end of the tube portion 21 is sealed and defines a bottom 21A and the other end is open and defines an opening portion 21B. The bottom 21A is shaped like a cone with the tip cut off. To perform centrifugal separation on a sample liquid 3, the opening portion 21B of the tube portion 21 that holds the sample liquid 3 is covered by the cap 22 and the tube portion 21 is inserted into one of the accommodation holes 10a of the angle rotor 1. Then, the centrifugal separation is performed.

Figure 6:
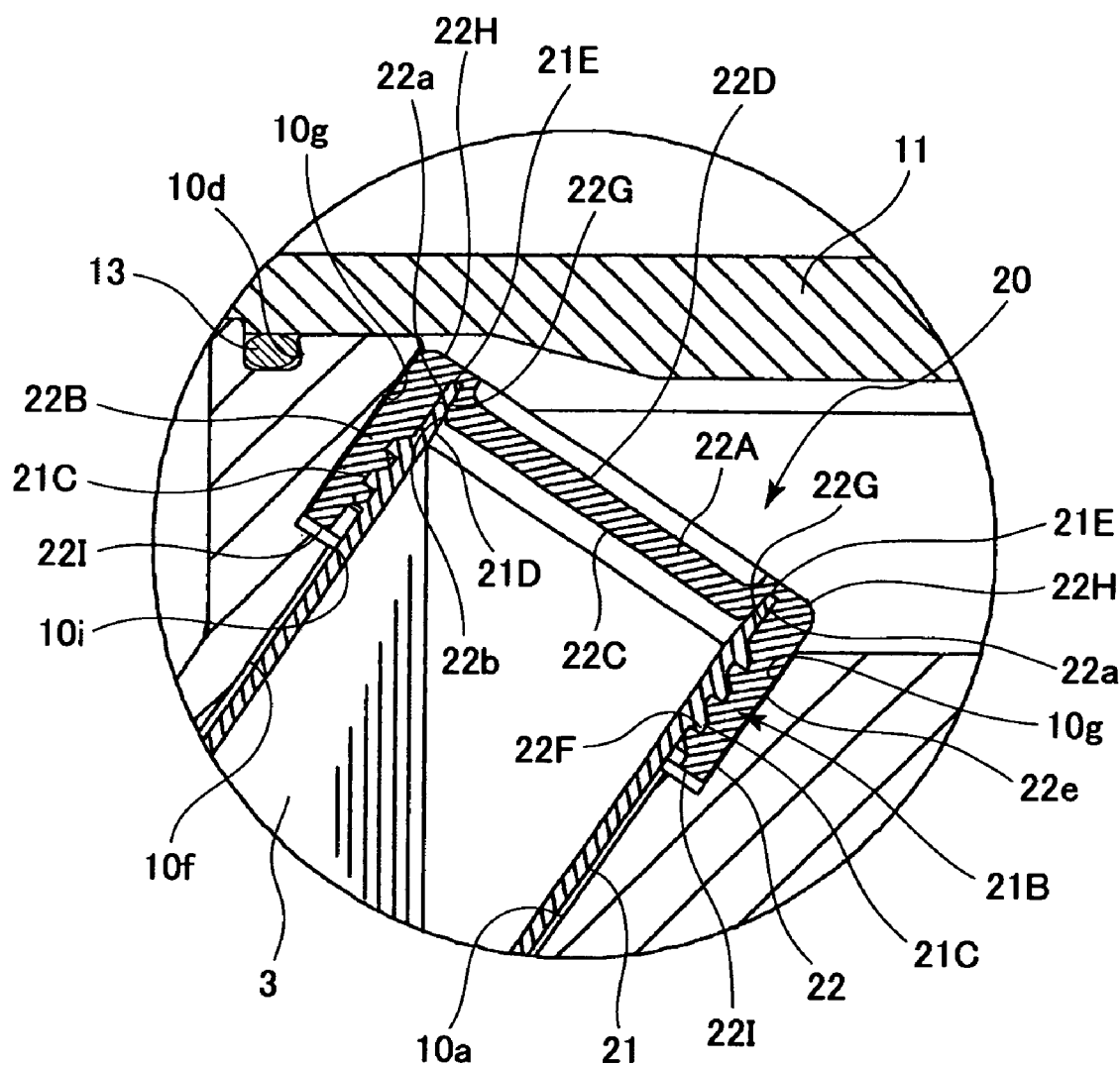
FIG. 6 is a magnified cross-sectional view of FIG. 5.

The tube portion 21 increases in diameter slightly and gradually from the bottom 21A with increasing proximity to the opening portion 21B. A male screw 21C having a saw-tooth shape in cross-section is provided at a position separated from an open edge 21E of the opening portion 21B. The male screw 21C is for screwingly engaging with a female screw 22F provided on the cap 22. As shown in FIGS. 6 and 9, a broad diameter portion 21D is provided at a position near the open edge 21E of the tube portion 21. The inner diameter at the broad diameter portion 21D gradually increases from the position of the male screw 21C that is nearest the open edge 21E to the position of the male screw 21C. The broad diameter portion 21D facilitates insertion of the portion of the tube portion 21 nearest the open edge 21E into a flange groove 22a of the cap 22 to be described later. A shown in FIG. 9, the inner surface of the tube portion 21 forms a smooth curved surface with no unevenness. For this reason, sediment separated from the sample liquid 3 by centrifugal separation can be easily removed from the tube portion 21.

The cap 22 includes a plate-shaped disk portion 22A and a flange portion 22B. The disk portion 22A has a disk shape of uniform thickness and includes a (lower) first surface 22C and a second (upper) surface 22D on opposite sides thereof. Said differently, the first surface 22C and the second surface 22D define the disk portion 22A. Both the first surface 22C and the second surface 22D are flat and circular. The flange portion 22B extends in the axial direction of the disk portion 22A from the outer peripheral surface of the first surface 22C. The female screw 22F has a saw-tooth shape in cross-section and is located at the inner periphery of the flange portion 22B at a position separated from the location where the flange portion 22B connects to the disk portion 22A. The disk portion 22A forms a right angle with the axial line of the flange portion 22B.

Normally, a cap is formed with escape grooves at the inner peripheral surface of the flange portion. The escape grooves are continuous with the groove section of the female screw of the cap. The escape grooves are formed for reasons of production and open in the direction in which inner diameter of the cap increases. However, no such escape grooves are formed in the cap of the present embodiment because such escape grooves form spaces between the cap and the tube. The open edge 21E could bend into the spaces when centrifugal force operates on the culture/centrifugal tube 20 during centrifugal separation.

An annular groove 22a is formed in the first surface 22C of the disk portion 22A at a position between the disk portion 22A and the flange portion 22B. The annular groove 22a extends into the disk portion 22A following the axial direction of the flange portion 22B. The opening portion 21B of the tube portion 21 engages in the annular groove 22a. An open side 22b of the annular groove 22a is continuous with and at the same level as the first surface 22C of the disk portion 22A. As shown in FIG. 6, an inner peripheral portion 22G of the flange portion 22B partially defines the annular groove 22a and is located near where the disk portion 22A and the flange portion 22B connect to each other. The inner peripheral portion 22G is formed to match the shape of the portion of the tube portion 21 near the open edge 21E. Because of this and the rigidity of the cap 22, the position near the open edge 21E and the near the connection position of the flange portion 22B are in intimate contact with no gaps therebetween when the opening portion 21B of the tube portion 21 is covered by the cap 22 and the portion near the open edge 21E is engaged in the annular groove 22a.

Figure 2:
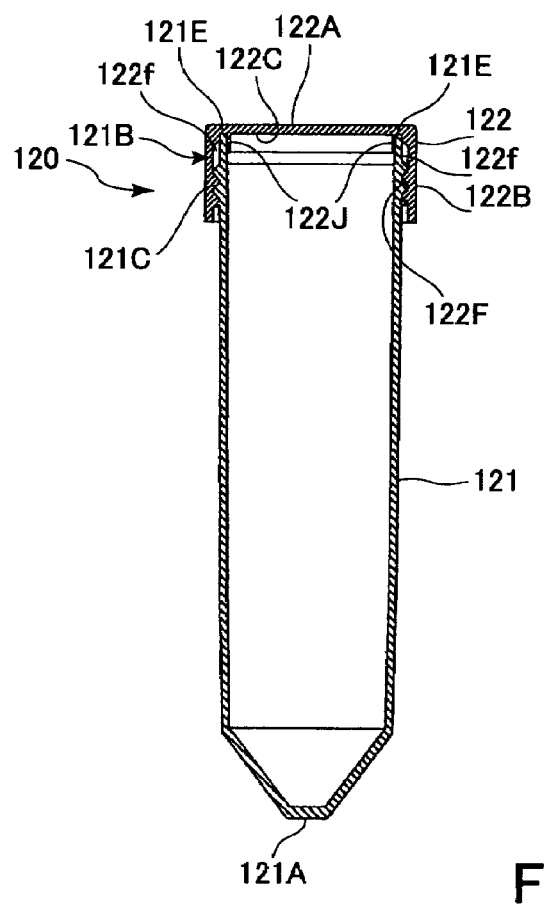
FIG. 2 is a cross-sectional view showing the culture centrifuge tube of FIG. 1.
Figure 3:
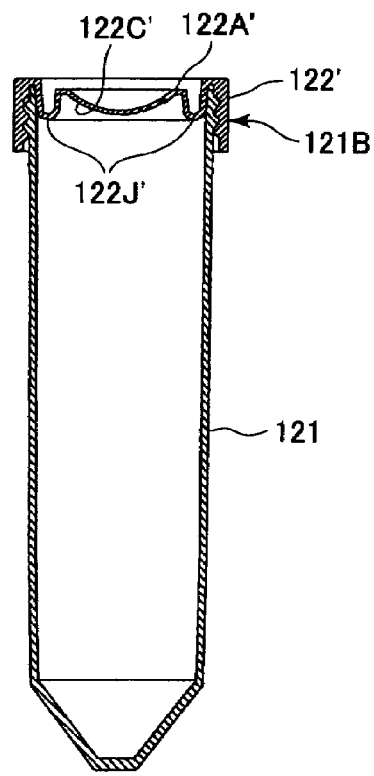
FIG. 3 is a cross-sectional view showing another conventional culture centrifuge tube.
Figure 4:
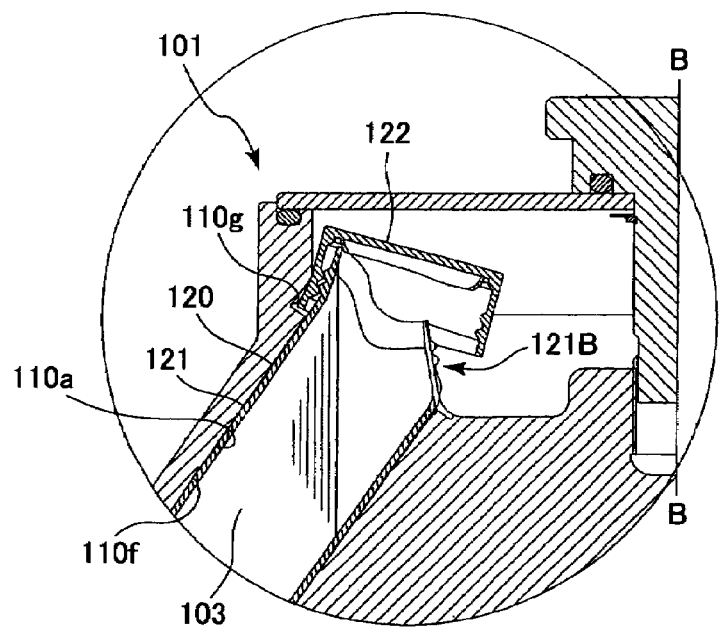
FIG. 4 is a cross-sectional view showing the culture centrifuge tube of FIG. 1 deformed under high centrifugal acceleration.

In contrast to the annular lip 122J of the conventional example shown in FIG. 2, the inner peripheral surface of the annular groove 22a is reinforced by the disk portion 22A being formed integrally with the inner peripheral surface of the annular groove 22a. Also, the cap 22 is made from polycarbonate. The combination of these two result in a configuration and material that insure intimate contact with the open edge 21E of the tube portion 21. The cap 22 has a uniform thickness and has a configuration and is made from a material that provide sufficient rigidity for insuring intimate contact between inner peripheral surface of the annular groove 22a and the opening portion 21B when the opening portion 21B is fitted into the annular groove 22a of the cap 22. Also, the configuration and material of the cap 22 provide sufficient rigidity to insure that the outer peripheral surface of the 22a of the cap 22 is in intimate contact with the opening portion 21B when the opening portion 21B is fitted in the annular groove 22a.

When the opening portion 21B of the tube portion 21 is covered by the cap 22, the open edge 21E is in intimate contact with the portion of the cap 22 where the flange portion 22B connects to the disk portion 22A. Therefore, the sample liquid 3 will not leak out from the culture/centrifugal tube 20 when the culture/centrifugal tube 20 is filled with a sample liquid 3 and cultivated in a shaking incubator or when a technician handles the culture/centrifugal tube 120. Also, when centrifugal separation are performed, the conventional problems of the open portion or the cap deforming, or the cap pulling away from the open portion, will not occur.

As shown in FIG. 6, the second surface 22D of the disk portion 22A is lower with respect to the axial direction of the flange portion 22B than a base portion 22H where the flange portion 22B connects to the disk portion 22A. With this arrangement, the second (upper) surface 22D of the disk portion 22A is positioned at a level substantially the same as that of the rim of the open end of the tube 21 when the cap 22 covers the open end. The disk portion 22A is formed only thick enough to provide proper stiffness. With this configuration, the cap 22 can be produced using the minimal amount of material. Therefore the cost of the culture/centrifugal tube 20, including the cap 22, can be reduced. Also, the cap 22 can be made lighter.

As shown in FIG. 8, a plurality of grooves 22c are formed in the outer periphery of the flange portion 22B of the cap 22. The grooves 22c extend in the axial direction of the flange portion 22B. The grooves 22c enable the user to grasp the cap 22 by hand and screw the cap 22 onto the tube portion 21 without the user's fingers slipping across the surface of the cap 22.

Here, the angle rotor 1 will be further explained. Although the accommodation holes 10a are formed in the angle rotor 1 to match the shape of the culture/centrifugal tube 20, it should be noted that the accommodation holes 10a are formed slightly larger than the outer contour of the culture/centrifugal tube 20. More specifically, the tube accommodation portion 10f is formed with a shape similar to the tube portion 21 so as to be able to accommodate and support the entire tube portion 21. When the culture/centrifugal tube 20 is inserted into one of the accommodation holes 10a, the tube accommodation portion 10f and the tube portion 21 are separated by a gap of about 0.1 mm to 0.5 mm in the radial direction of the accommodation holes 10a.

With this configuration, the amount that the tube portion 21 expands under the pressure applied by the sample liquid 3 during centrifugal separation can be properly suppressed. Expansion of the tube portion 21 can be suppressed to a range that does not cause problems even though the tube portion 21 is made from a material that shows a certain elongation characteristic. Also, this configuration facilitates insertion and removal of the culture/centrifugal tube 20 into and out of the accommodation holes 10a. Because the accommodation holes 10a are formed to match the shape of the culture/centrifugal tube 20, each of the accommodation holes 10a are formed with a bottom 10h with a shape similar to the bottom 21A of the tube portion 21. This configuration suppresses the amount that the culture/centrifugal tube 20 deforms under the liquid pressure generated by centrifugal force.

The cap accommodation portion 10g of each of the accommodation holes 10a is formed with a shape similar to a portion of the cap 22. More specifically, the cap accommodation portion log is formed in a tubular shape that encompasses the flange portion 22B of the cap 22 entirely at a cap-encompassing region 22e shown in FIG. 6. The cap-encompassing region 22e extends from the free end 22I of the flange portion 22B in the axial direction of the flange portion 22B to a predetermined position somewhere in the direction toward the base portion 22H. As shown in the lower right portion of FIG. 6, the cap-encompassing region 22e extends in the axial direction of the flange portion 22B to only about 75% of the length of the cap 22 in the axial direction of the flange portion 22B. It should be noted that the side of the flange portion 22B shown in the upper left of FIG. 6 extends to the same length as (is 100% the length of) the flange portion 22B of the cap 22. However, only this portion of the flange portion 22B does this. That is, the cap 22 is completely encompassed by the flange portion 22B only within the 75%-axial-length cap-encompassing region 22e of the flange portion 22B.

A gap of about 0.1 mm to 0.3 mm is formed between the cap 22 and the cap accommodation portion 10g in the radial direction of the accommodation holes 10a. With this configuration, the cap 22 can be properly supported so that the cap 22 does not deform during centrifugal separation.

As shown in FIG. 6, when the culture/centrifugal tube 20 is inserted in the accommodation hole 10a, a slight gap is formed between the free end 22I of the cap 22 and a position 10i where the cap accommodation portion 10g and the tube accommodation portion 10f of the accommodation holes 10a connect. This gap is formed because the distance in the axial direction of each of the accommodation hole 10a from the position 10i to the bottom 10h of the tube accommodation portion 10f is shorter than the distance in the axial direction of the tube portion 21 from the free end 22I of the flange portion 22B of the cap 22 to the bottom 21A of the tube portion 21.

As described above, the tube accommodation portion 10f and the tube portion 21 are separated by a gap of about 0.1 mm to 0.5 mm in the radial direction of the accommodation holes 10a. Therefore, the tube portion 21 of the culture/centrifugal tube 20 expands under pressure from the sample liquid 3 during centrifugal separation. In addition, the tube portion 21 will also shrink in the axial direction of the culture/centrifugal tube 20. At this time, the free end 22I of the cap 22 and the connection position 10i will not abut against each other because the slight gap formed between the free end 22I of the cap 22 and the connection position 10i absorbs the shrinkage.

If the free end 22I of the cap 22 and the connection position 10i abutted against each other, then the cap 22 might be pulled off the tube portion 21 by force generated as the centrifugal force pulls the tube portion 21 toward the bottom 10h of the tube accommodation portion 10f. However, because the free end 22I of the cap 22 and the connection position 10i will not abut against each other, no such force is generated and the cap 22 will not be pulled from the tube portion 21. Accordingly, the size of the gap desired between the free end 22I of the cap 22 and the connection position 10i when the culture/centrifugal tube 20 is initially set in the accommodation hole 10a is determined by the shrinkage allowance in the axial direction of the tube portion 21. This shrinkage allowance is determined by the gap between the tube portion 21 and the tube accommodation portion 10f of the accommodation hole 10a.

While the invention has been described in detail with reference to the specific embodiments thereof, it would be apparent to those skilled in the art that various changes and modifications may be made therein without departing from the spirit of the invention.

Figure 10:
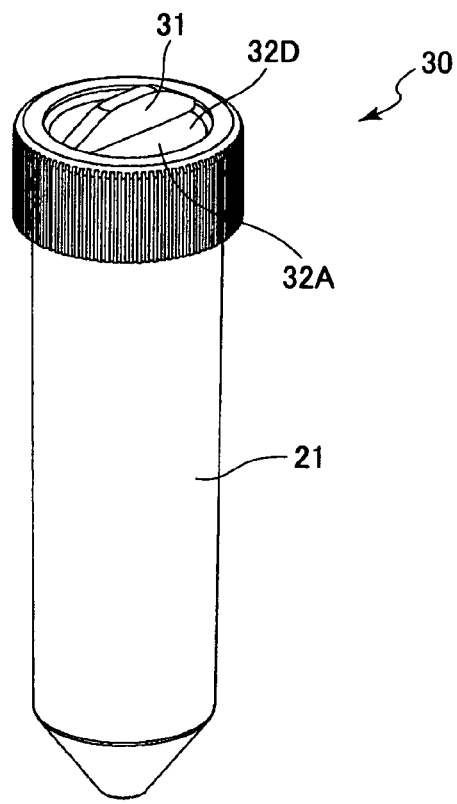
FIG. 10 is a perspective view showing a culture centrifuge tube according to a modification of the embodiment.

For example, both the first and second surfaces 22C, 22D of the disk portion 22A are described in the embodiment as being flat. However, this need not be the case. For example, FIG. 10 shows a culture/centrifugal tube 30 with a disk portion 32A having a second surface 32D formed with an integral handle 31. With this configuration, the culture/centrifugal tube 30 can be easily removed from the accommodation holes 10a of the rotor body 10 without using some sort of tool.

Figure 11:
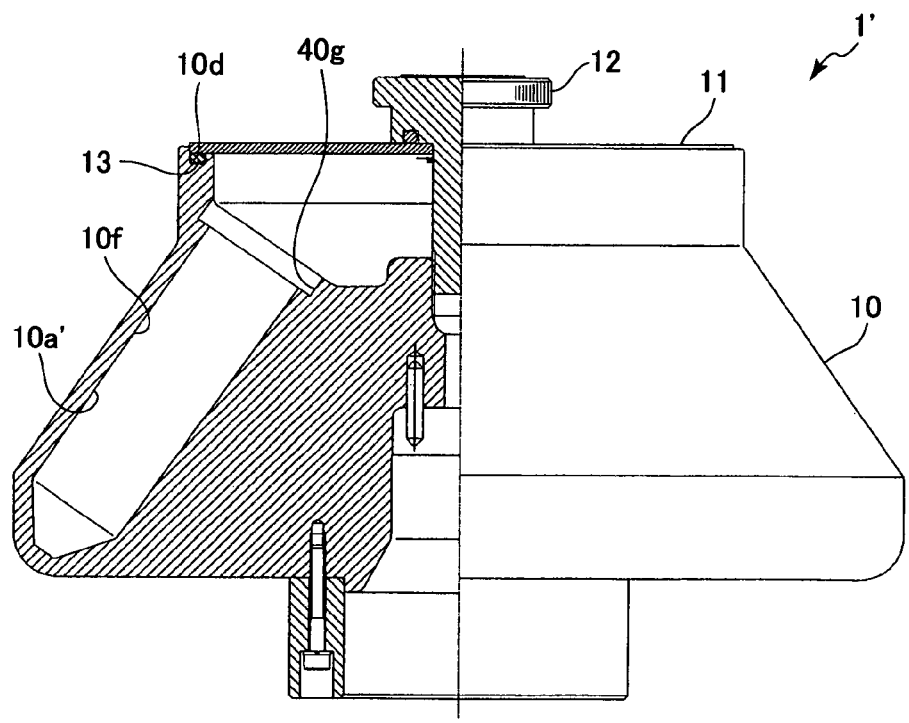
FIG. 11 is a side view partially in cross-section showing an angle rotor according to a modification of the embodiment.

Further, in the embodiment, the cap-encompassing region 22e is described as extending to only about 75% of the length of flange portion 22B of the cap 22. However, the length of the cap-encompassing region 22e is not limited to this value. FIG. 11 shows an angle rotor 1' with a cap accommodation portion 40g that has a length in the axial direction that is only 40% or more of flange portion 22B of the cap 22. It should be noted that there is a need to set the length of the cap accommodation portion 40g to 40% or more of the flange portion 22B of the cap 22 in order to sufficiently prevent the cap from deforming or moving radially outward under pressure from the sample liquid and the centrifugal force during rotation of the angle rotor 1'.

Because only a small gap exists between the cap and the cap accommodation portion 40g, the cap accommodation portion 40g blocks the cap from moving radially away from the rotation axis. By setting the length of the cap accommodation portion 40g to 40% or more of the flange portion 22B of the cap 22, a greater amount of the cap 22 is exposed from the cap accommodation portion 40g. This makes the cap 22 easier for the user to grasp, so that the culture/centrifugal tube 20 is easier to insert into and remove from the accommodation holes 10a'.

The bottom 21A of the tube portion 21 is described in the embodiment as having the shape of a cone with the tip cut off. However, the bottom of the tube portion is not limited to this shape and, for examples could be a hemispherical instead.

The tube portion 21 and the cap 22 are described in the embodiment as being made from polycarbonate. However, the tube portion and the cap of the culture/centrifugal tube can be made from a plastic such as polypropylene or polyester. When the culture/centrifugal tube is made from any of these materials, the culture/centrifugal tube can be easily and inexpensively produced.

The embodiment describes that the second (upper) surface 22D of the disk portion 22A is lower with respect to the axial direction of the flange portion 22B than the base portion 22H where the flange portion 22B connects to the disk portion 22A. However, the second surface could be level with the base portion so that the cap is easier to produce.

The male screw 21C formed in the tube portion 21 and the female screw 22F formed in the cap 22 are described in the embodiment as having a having a saw-tooth shape in cross-section. However, this is not a limitation to the present invention. For example, the screws could be formed in the shape of a normal equilateral triangle in cross-section.

The embodiment describes that the tube accommodation portion 10f and the tube portion 21 are separated by a gap of about 0.1 mm to 0.5 mm in the radial direction of the accommodation holes 10a when the culture/centrifugal tube 20 is inserted into one of the accommodation holes 10a. However, the gap should be set to a smaller value if the tube portion 21 is made from a plastic with a low elongation characteristic.

The embodiment describes that no escape grooves are formed in the bottom of the screw groove of the female screw 22F. However, small-width escape grooves could be formed.

What is claimed is:

1. A culture/centrifugal tube that is used to hold a sample liquid and inserted into an accommodation space in an angle rotor of a centrifuge, the angle rotor rotating to subject the culture/centrifugal tube to centrifugal force, the culture/centrifugal tube comprising:
   a plastic vessel including:
   a base end that is closed;
   an open end that is open and opposite from the base end, the open end having an outer periphery and a rim, the outer periphery being formed with a spiral-shaped male screw and the rim defining an opening; and
   a side wall extending between the base end and the open end, the side wall and the base end defining an inside of the plastic vessel; and
   a plastic cap for covering the opening of the vessel, the cap including:
   a disk portion having an upper surface, a bottom surface and an outer peripheral surface, the bottom surface facing downward and having a perimeter, the outer peripheral surface extending upwardly from the perimeter of the bottom surface; and
   an annular portion connected to a portion of the outer peripheral surface of the disk portion and extending downward, the annular portion having an inner peripheral surface formed with a spiral-shaped female screw that engages with the male screw of the vessel to seal the inside of the vessel, an annular groove being defined between the annular portion and the outer peripheral surface of the disk portion, the annular groove extending downward and opening at a position level with the bottom surface of the disk portion, the open end of the vessel extending into the annular groove with the open end of the vessel in abutment against the disk portion when the male screw and the female screw are fully engaged, and
   wherein the upper surface is positioned at a level substantially the same as that of the rim of the open end of the vessel when the cap covers the open end.

2. The culture/centrifugal tube as claimed in claim 1, wherein the cap includes a flange portion extending in an axial direction of the disk portion, and the upper surface of the disk portion is lower, with respect to an axial direction of the flange portion, than a base portion of the annular portion of the cap.

3. The culture/centrifugal tube as claimed in claim 1, wherein the disk portion of the cap further has
   a handle formed integral to the upper surface.

4. The culture/centrifugal tube as claimed in claim 1, wherein the annular portion of the cap further has an outer peripheral surface formed with a plurality of parallel grooves all extending downward.

5. The culture/centrifugal tube as claimed in claim 1, wherein at least one of the vessel and the cap are formed from at least one material selected from the group consisting of polypropylene, polystyrene, and polycarbonate.

6. The culture/centrifugal tube as claimed in claim 1, wherein the male screw formed in the outer periphery of the open end starts from a position separated downward from the rim of the open end, the female screw being formed on the inner peripheral surface of the annular portion at a position separated from a position where the annular portion is connected to the disk portion, the outer periphery of the open end of the vessel being in intimate contact with the inner peripheral surface of the annular portion along a surface between the edge of the open end and the position where the male screw starts.

7. The culture/centrifugal tube as claimed in claim 1, wherein the open end of the vessel has an inner periphery that gradually increases in diameter with proximity to the edge of the open end.

8. The culture/centrifugal tube as claimed in claim 1, wherein the cap is provided with sufficient stiffness for securing a sealed condition between the annular portion of the cap and the open end of the vessel engaged in the groove.

9. The culture/centrifugal tube as claimed in claim 1, wherein the disk portion and the annular portion are integral with each other.

10. An angle rotor for receiving a culture/centrifugal tube and for use in a centrifuge, the centrifuge having a motor that generates force for rotating the angle rotor and subjecting the culture/centrifugal tube to centrifugal force, the culture/centrifugal tube including:
    a plastic vessel including:
    a base end and an open end at opposite ends thereof, the base end being closed and the open end having an outer periphery and a rim, the outer periphery being formed with a spiral-shaped male screw and the rim defining an opening; and
    a side wall extending between the base end and the open end, the side wall and the base end defining an inside of the plastic vessel; and
    a plastic cap for covering the opening of the vessel, the cap including:
    a disk portion having an upper surface, a bottom surface and an outer peripheral surface, the bottom surface facing downward and having a perimeter, the outer peripheral surface extending from the perimeter of the bottom surface; and
    an annular portion connected to a portion of the outer peripheral surface of the disk portion and extending downwards the annular portion having an inner peripheral surface formed with a spiral-shaped female screw that engages with the male screw of the vessel to seal the inside of the vessel, an annular groove being defined between the annular portion and the outer peripheral surface of the disk portion, the annular groove extending downward and opening at a position level with the bottom surface of the disk portion, the open end of the vessel extending into the annular groove with the open end of the vessel in abutment against the disk portion when the male screw and the female screw are fully engaged, wherein the upper surface is positioned at a level substantially the same as that of the rim of the open end of the vessel when the plastic cap covers the open end;

the angle rotor comprising:

a connection member for connecting to the motor of the centrifuge; and an accommodation portion that is rotated about a rotation axis through the connection member by the drive force from the motor, the accommodation portion including an accommodation hole forming portion that defines an accommodation hole accommodating the culture/centrifugal tube, the accommodation hole extending in a direction at an angle to the rotation axis, the accommodation hole forming portion including a vessel accommodating portion that accommodates the vessel and a cap accommodating portion that accommodates the cap, the vessel accommodating portion having a smaller diameter than the cap accommodating portion, the cap accommodating portion including a region that extends a predetermined distance in the direction, the region entirely encompassing a corresponding portion of the outer periphery of the annular portion of the cap.

11. The angle rotor as claimed in claim 10, wherein the annular portion of the cap extends to a length in the direction, the predetermined distance in which the region of the cap accommodating portion extends in the direction being 40% or more of the length of the annular portion.

12. The angle rotor as claimed in claim 10, wherein the accommodation vessel is formed with:

a step between the vessel accommodating portion and the cap accommodating portion; and a bottom at a side of the vessel accommodating portion opposite from the cap accommodating portion, the bottom being adapted for receiving the base end of the vessel, the vessel accommodating portion being formed with a distance from the step to the bottom that is shorter than a distance separating a base side edge of the annular portion of the cap from the base end of the vessel.

13. The angle rotor as claimed in claim 10, wherein the disk portion and the annular portion are integral with each other.

* * * * *